US008899225B2

United States Patent
Bosel

(10) Patent No.: US 8,899,225 B2
(45) Date of Patent: Dec. 2, 2014

(54) PERCUTANEOUS DILATIONAL DEVICE HAVING BALLOON RETENTION MECHANISM

(75) Inventor: Christopher D. Bosel, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 989 days.

(21) Appl. No.: 13/009,017

(22) Filed: Jan. 19, 2011

(65) Prior Publication Data

US 2012/0180787 A1 Jul. 19, 2012

(51) Int. Cl.
*A61M 11/00* (2006.01)
*A61M 16/04* (2006.01)
*A61M 29/02* (2006.01)
*A61M 25/10* (2013.01)

(52) U.S. Cl.
CPC ... *A61M 16/0472* (2013.01); *A61M 2025/1047* (2013.01); *A61M 16/0488* (2013.01); *A61M 2025/1086* (2013.01); *A61M 2025/1031* (2013.01); *A61M 25/1011* (2013.01); *A61M 29/02* (2013.01); *A61M 25/1018* (2013.01); *A61M 25/1002* (2013.01); *A61M 16/0434* (2013.01)
USPC ............. 128/200.26; 128/207.14; 128/207.15

(58) Field of Classification Search
CPC ............ A61M 16/0488; A61M 16/04; A61M 16/0472
USPC ............. 128/200.26, 207.14, 207.15, 207.29
See application file for complete search history.

(56) References Cited

U.S. PATENT DOCUMENTS

| | | | | |
|---|---|---|---|---|
| 3,810,474 | A * | 5/1974 | Cross | 128/207.15 |
| 4,340,046 | A * | 7/1982 | Cox | 128/207.17 |
| 5,653,230 | A * | 8/1997 | Ciaglia et al. | 128/207.15 |
| 5,720,726 | A * | 2/1998 | Marcadis et al. | 604/103.08 |
| 6,971,382 | B1 * | 12/2005 | Corso | 128/200.26 |
| 7,036,510 | B2 | 5/2006 | Zgoda et al. | 128/207.29 |
| 7,195,017 | B2 * | 3/2007 | Tanaka | 128/207.14 |
| 7,591,830 | B2 * | 9/2009 | Rutter | 606/191 |
| 8,424,534 | B2 * | 4/2013 | Lyons et al. | 128/898 |
| 8,601,633 | B2 * | 12/2013 | Vazales et al. | 15/104.05 |
| 8,636,010 | B2 * | 1/2014 | Nelson et al. | 128/207.15 |
| 2005/0183729 | A1 | 8/2005 | Fischer, Jr. | 128/207.29 |
| 2011/0290245 | A1 * | 12/2011 | Cuevas et al. | 128/200.26 |
| 2013/0000635 | A1 * | 1/2013 | Curley et al. | 128/200.26 |

* cited by examiner

*Primary Examiner* — Steven Douglas
(74) *Attorney, Agent, or Firm* — Brinks Gilson & Lione

(57) ABSTRACT

A device for dilating an opening through the tracheal wall of a patient includes a loading dilator. A balloon catheter is received in the lumen of the dilator such that the balloon extends distal to the loading dilator distal end. The balloon is configured to radially dilate a portion of the tracheal wall upon inflation. The balloon includes retention structure along its outer surface such that upon inflation, the retention structure inhibits dislodgement of the balloon when the balloon is positioned across the tracheal wall. The retention structure may comprise a pair of spaced elements radially projecting from the outer surface of the balloon, and spaced along the outer surface such that each of the elements is disposed at an opposite side of the tracheal wall when the balloon is positioned along the tracheal wall opening.

20 Claims, 3 Drawing Sheets

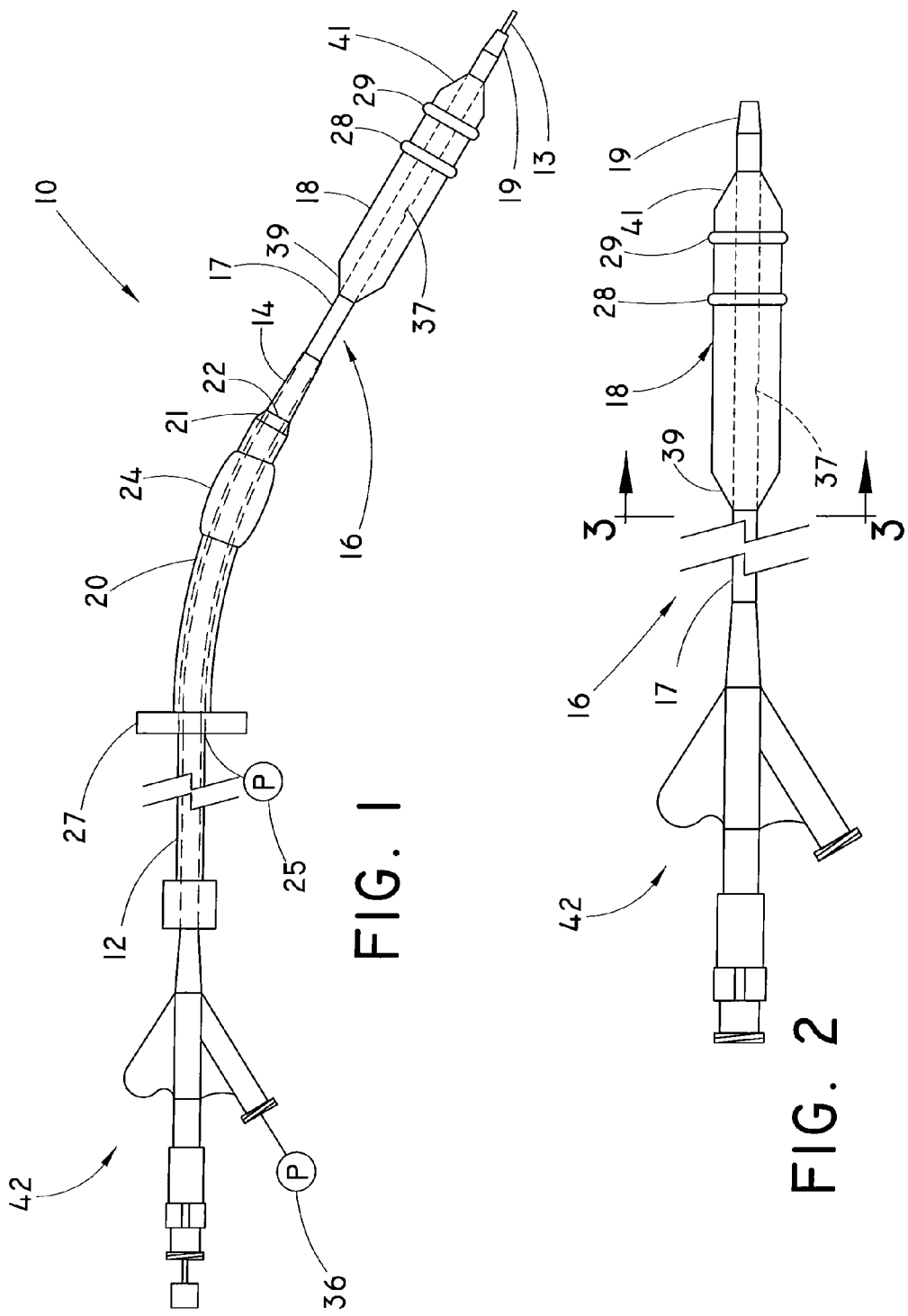

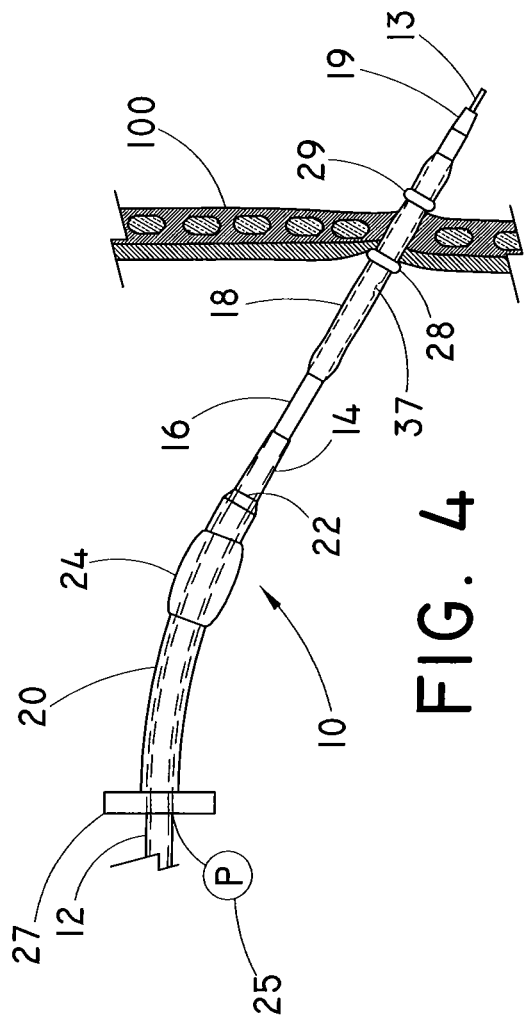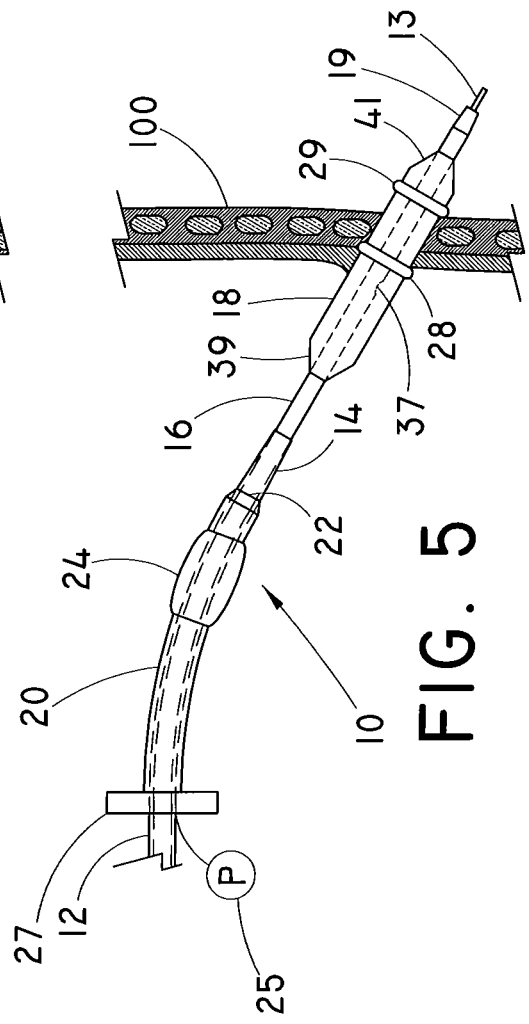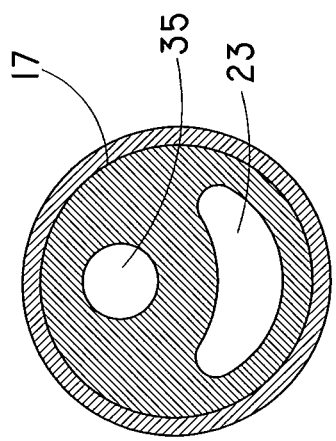

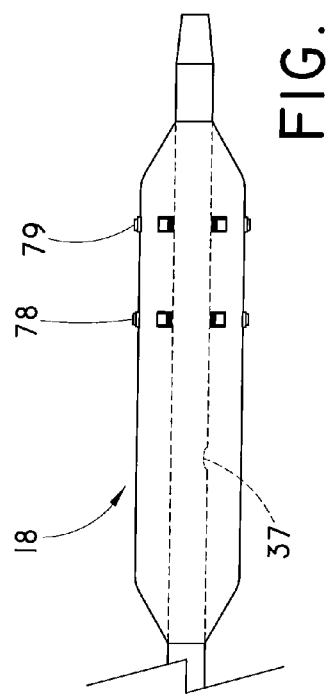
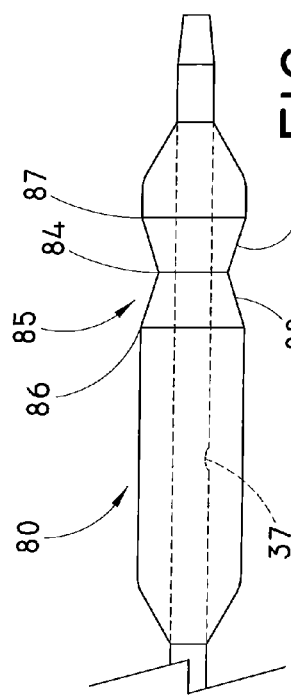

PERCUTANEOUS DILATIONAL DEVICE HAVING BALLOON RETENTION MECHANISM

BACKGROUND

1. Technical Field

This invention relates generally to a device for dilating an opening through a wall of a patient's air passageway. More particularly, the invention relates to a dilational device having a balloon retention mechanism for maintaining a position of the balloon across the air passageway wall during dilation of the passageway.

2. Background Information

The restoration of an adequate air passageway is the first critical step in maintaining the ability of a seriously ill or injured patient to breathe, or in performing resuscitation on a patient unable to breathe. Endotracheal intubation (the placement of a tube through the nostrils or mouth and into the trachea itself) is generally considered the preferred method for establishing an air passageway when the trachea, nostrils and/or mouth are free of obstruction. When an obstruction is present, however, endotracheal intubation is often not possible, and some other passageway for airflow must be established.

The most direct way to provide an air passageway under these circumstances is to form an opening in the tracheal wall, and once formed, to maintain the opening by inserting a tracheostomy tube therethrough. Conventional tracheostomy tubes generally include an open distal aperture, and a circumferential inflatable cuff to provide a seal between the tracheal wall and the tracheostomy tube.

Several methods and devices are known for forming or enlarging an opening in a tracheal wall. Each method is subject to certain advantages and disadvantages. For example, tracheostomy and cricothyrotomy procedures have been performed by using a scalpel to make an incision in the neck. Such procedures entail a high degree of surgical skill to perform successfully, particularly since it is vital to locate and avoid unintentional severing of the blood vessels in the area. These procedures can even require the surgeon to cut through several blood vessels and ligate (tie) them to the trachea, in order to achieve an adequately large opening. The length of time needed to perform these procedures (often on the order of half an hour) is poorly suited to emergency treatment, when prompt restoration of the air passageway is critical. Moreover, the use of a scalpel to fully form an opening potentially causes undue trauma to the tissues surrounding the opening, and can result in the formation of an unduly large or oversized opening in the soft tissue of the neck.

To minimize such trauma, it has been found desirable to initially incise only a small opening, and thereafter enlarge the opening with further dilation. For example, one technique for dilating an opening includes the use of a wire guide to facilitate the introduction of a dilator into the trachea. This technique involves making a small incision with a scalpel, and inserting a needle and wire guide through the incision. The needle is removed, and a tapered, elongated, tubular dilator is positioned over the wire guide and introduced into the trachea. One drawback of this technique is that the tubular dilator must thereafter be withdrawn, and a loading dilator/tracheostomy tube combination must then be inserted over the wire guide. Even though intended to be performed in an emergency situation, the technique entails the sequential manipulation of several devices by the physician, which is time consuming and complicates the procedure.

In another procedure, an opening formed by the needle is dilated by the use of a device having a handle and a nose, the nose extending laterally from the axis of the handle. The nose has two jaws that spread apart for separating the tissue surrounding the opening, and the device is introduced into the trachea by positioning the elongated, tapered nose over the wire guide. While this type of device may offer more powerful dilation than elongated tubular dilators, a problem with this device is that the unguarded nose must be inserted into the trachea with precision, and must be manipulated at an angle to avoid perforating the posterior tracheal wall.

Another prior art technique for dilating an opening is the use of a tapered, elongated, tubular dilator, or a series of tapered dilators having increasingly larger diameters. Although such dilators are effective for forming a suitably-sized opening in the tracheal wall, each dilator presents a pointed distal end to the posterior tracheal wall when introduced into the trachea. The risk of injury to the trachea is compounded by the toughness of the tracheal membrane, which resists the introduction of medical devices. Introducing these elongated dilators typically requires the application of considerable force. Although a hydrophilic coating may be applied to the dilator to reduce the amount of force required to insert the dilator, a physician must still exert a downward force to push the dilator into the trachea, and yet avoid puncturing the posterior tracheal wall.

Prior art devices described in U.S. Pat. Nos. 5,653,230 and 7,036,510, both incorporated by reference herein, describe devices and methods for radially dilating a tracheal opening. A catheter having a polymeric inflatable balloon at the distal end of the catheter is provided. The uninflated balloon is positioned across an opening formed in the airway wall. The balloon is slowly inflated, thereby radially dilating the opening in the tracheal wall to form an ostomy of suitable size to permit insertion of a tracheostomy tube. Since these devices permit the radial enlargement of an opening, they eliminate the necessity of exerting the downward or axial push force required by many existing devices.

Although the devices described in the '230 and '510 patents are generally effective for radially dilating the opening in the tracheal wall, it is possible that the balloon may slip into or out of the trachea during inflation. Such slippage may occur, for example, as a result of inflation forces acting upon the balloon, and/or due to the resistance exerted by the tissue being dilated by the inflating balloon. When this occurs, the user generally must deflate the balloon, reposition it across the tracheal wall, and repeat the balloon inflation. Since these steps involve providing, or maintaining, an adequate airway for the patient, any additional steps that must be carried out to achieve proper positioning of the tracheostomy tube are inherently undesirable.

It would be desirable to provide a dilational device capable of radially dilating an opening in a tracheal wall, and that is structured in a manner to inhibit slippage or other undesired movement of the balloon during dilation.

BRIEF SUMMARY

The present invention addresses the shortcomings of the prior art. In one form thereof, a device is provided for dilating an opening through a tracheal wall of a patient. A balloon catheter has a proximal end, a distal end, and includes an inflatable balloon disposed at the distal end. The inflatable balloon is configured to dilate a portion of the tracheal wall upon inflation. The balloon comprises retention structure along its outer surface such that upon inflation of the balloon, the retention structure inhibits a dislodgement of the balloon when the balloon is positioned across the tracheal wall. The retention structure may comprise a pair of spaced elements radially projecting from the outer surface of the balloon, wherein the elements are spaced along the balloon outer surface such that each of the elements is disposed at an opposite side of the tracheal wall when the balloon is inserted into the tracheal wall opening. The balloon catheter may be received in a loading dilator such that the balloon catheter distal end extends distal to the loading dilator distal end.

In another form thereof, a method is provided for dilating an opening through a tracheal wall of a patient. A dilation device comprises a loading dilator having a lumen extending therethrough, and a balloon catheter received in the dilator lumen. The balloon catheter has a distal end extending distal to a distal end of the loading dilator. The balloon catheter includes an inflatable balloon at the distal end, the inflatable balloon being structured to dilate a portion of the tracheal wall upon inflation. The balloon comprises retention structure along the outer surface for inhibiting a dislodgement of the balloon upon inflation when positioned across the tracheal wall. An end of a wire guide is inserted through the tracheal wall opening, and the dilation device having the balloon in an uninflated condition is advanced over the wire guide until the balloon retention structure is positioned across the tracheal wall. The balloon is then inflated to dilate the tracheal wall opening.

In yet another form thereof, a device provides an airway through a tracheal wall of a patient. A loading dilator has an outer surface, a tapered distal end, and having a lumen extending therethrough. A balloon catheter is receivable in the dilator lumen such that the distal end of the balloon catheter extends distal to the distal end of the loading dilator. The balloon catheter includes an inflatable balloon at its distal end, wherein the inflatable balloon is structured to atraumatically dilate a portion of the tracheal wall upon inflation. The balloon comprises a pair of spaced elements radially projecting from the balloon outer surface, and spaced along the balloon outer surface such that each of the elements is disposed at an opposite side of the tracheal wall when the uninflated balloon is inserted into the tracheal wall opening for dilation. A tracheostomy tube is received on the outer surface of the loading dilator.

BRIEF DESCRIPTION OF THE DRAWINGS

FIG. 1 is a side view of a device for dilating an opening in a tracheal wall of a patient according to an embodiment of the present invention, and showing a tracheostomy tube carried on the device;

FIG. 2 is a side view of the balloon catheter;

FIG. 3 is an enlarged cross-sectional view taken along line 3-3 of FIG. 2;

FIG. 4 is a view of a dilation procedure carried out using a preferred embodiment of the inventive device, wherein the balloon is in an uninflated condition;

FIG. 5 is a view of the dilation procedure as shown in FIG. 4, wherein the balloon is in an inflated condition;

FIG. 6 illustrates an alternative embodiment of retention rings disposed along the outer surface of the balloon; and FIG. 7 illustrates another alternative embodiment of a balloon, wherein the balloon includes a groove along its outer surface.

DETAILED DESCRIPTION OF THE DRAWINGS AND THE PRESENTLY PREFERRED EMBODIMENTS

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention relates to a dilational device comprising a balloon catheter equipped with retention features for minimizing a possibility of slippage or other unintended dislodgement of the balloon during dilation of an opening, such as an opening through the tracheal wall of the patient. In the following discussion, the terms "proximal" and "distal" will be used to describe the opposing axial ends of the device, as well as the axial ends of various component features. The term "proximal" is used in its conventional sense to refer to the end of the device (or component thereof) that is closest to the operator during use of the device. The term "distal" is used in its conventional sense to refer to the end of the device (or component thereof) that is initially inserted into the patient, or that is closest to the patient during use.

FIG. 1 illustrates one embodiment of a percutaneous dilational device 10 for forming an opening, or ostomy, in a tracheal wall. In this embodiment, the device 10 comprises a hollow dilator tube 12 having a tapered distal end 14, and a balloon catheter 16. The balloon catheter 16 includes a catheter shaft 17, and an inflatable balloon 18 positioned at a distal portion of the shaft. The balloon catheter is coaxially carried by and disposed within a throughbore of the dilator tube 12. A conventional manifold 42 may be provided at the proximal end of the balloon catheter in well-known fashion. FIG. 1 also illustrates the presence of a tracheostomy tube 20 carried by the dilator tube.

The dilator tube 12 and the balloon catheter 16 are comprised of medical grade, synthetic materials commonly used in the art for such purposes. Balloon catheter shaft 17 is typically composed of a relatively flexible and slightly elastic material, such as nylon (polyamide), polyethylene, or polyurethane. The dilator tube 12 is preferably composed of a somewhat more rigid but somewhat resilient material. The dilator tube may be formed from the same polymer as the balloon catheter shaft, but with a thicker wall or utilizing a higher durometer grade.

Balloon 18 is preferably formed of a flexible but inelastic material, such as PET or nylon. The balloon preferably has a generally cylindrical shape upon inflation, and includes tapered proximal end 39 and distal end 41. The inflated diameter of the balloon 18 is selected in view of the size of the tracheal wall opening to be formed. The balloon 18 is typically between about 60 and 120 mm long, but the balloon length may be longer, or shorter, than this if desired. For use herein, the balloon 18 can conveniently have an operating pressure of between about 8 and 14 (preferably about 11) atmospheres, and a burst pressure of between about 20 and 26 (preferably about 23) atmospheres. Those skilled in the art will appreciate that balloon operating pressures and burst pressures may be varied based upon a myriad of factors, including balloon composition and dimension, patient size, etc., and the pressures recited herein are only intended to represent examples of pressures that may be appropriate for use with a particular patient.

Further description of balloon catheters and dilator tubes commonly used for dilating openings in a tracheal wall is provided in the incorporated-by-reference '230 and '510 patents, and need not be further described herein. Conventional balloon catheters and dilator tubes are available commercially from a variety of sources, including Cook Medical, of Bloomington, Ind.

The balloon portion of the balloon catheter is equipped with retention features for minimizing a possibility of slippage or other unintended dislodgement of the balloon during use for dilating an opening. As shown in FIGS. 1 and 2, the retention features may comprise rings 28, 29 formed along the outer surface of the balloon. In a preferred embodiment, rings 28, 29 have a radial extension of about 1-5 mm beyond the outer surface of balloon 18. Thus, for example, when balloon 18 has an outer diameter of about 16 mm, the outer diameter of rings 28, 29 will be between about 18 and 26 mm. The rings are preferably spaced about 10-25 mm apart, and more preferably about 15-20 mm, along the surface of the balloon. The spacing between the rings is generally not crucial, as long as the rings are spaced at least as far apart as the thickness of the tissue at the body opening, e.g., the thickness of the tracheal wall. Typically, an additional spacing beyond the thickness of the tissue (tracheal wall) is desirable to allow for various angles of passage of the balloon through the wall.

Rings 28, 29 may be formed on balloon 18 at the time of formation of the balloon. Thus, for example, when a balloon is to be formed by blow molding, a parison made from the polymeric tubing material is positioned in a mold having an interior cavity of appropriate configuration to form the balloon and rings. The parison is then exposed to heat and pressure in the mold in conventional manner. Many commercial producers are readily able to mold balloons to a desired shape, such as Interface Catheter Solutions, of Laguna Niguel, Calif. Those skilled in the art will appreciate that other means of forming a balloon having rings as described may be substituted.

Dilator tube 12 and balloon catheter 16 are preferably adapted for advancement along a wire guide. As shown in the sectional view of FIG. 3, balloon catheter shaft 17 includes a longitudinal throughbore 35 dimensioned to receive a wire guide 13 therein. Wire guide 13 will typically have a diameter of about 0.035 to 0.052 inch, and thus, throughbore 35 must be dimensioned to accommodate the wire guide, while permitting free movement of the wire guide therethrough. The tip 19 of the catheter shaft 17 is preferably tapered in the distal direction but maintains an opening of sufficient size to allow entry of the wire guide into the throughbore 35. Catheter shaft 17 also includes a longitudinally extending bore 23 (FIG. 3) for supplying a fluid under pressure for inflating the balloon 18. The bore 23 fluidly interconnects the interior space of balloon 18 with a supply of pressurized fluid 36 in well-known fashion, the fluid supply 36 being schematically indicated in FIG. 1 by the symbol "P". One or more ports 37 in catheter 16 are open to the interior of balloon 18 to complete the fluid communication of the balloon 18 with the fluid supply 36. Preferably, the fluid provided by the fluid supply 36 is a conventional fluid for such purposes, such as saline solution or sterile water, supplied under an appropriate pressure (e.g., about 11 atmospheres) to atraumatically dilate the tracheal wall to form a suitable opening. Fluid supply to inflatable balloons for use in medical devices is well known in the art, and no further discussion of this aspect of the balloon catheter is necessary.

The purpose of forming an opening in the tracheal wall is to allow the insertion of a tracheostomy tube 20 through the tracheal wall, so as to establish an air passageway for the patient. The device 10 as described can be used for establishing an opening for the insertion of a separate tracheostomy tube 20 standing alone, which may be separately inserted following dilation of the opening as described herein. However, the device 10 will preferably include the tracheostomy tube 20 as well, wherein the tube 20 is coaxially carried on the dilator tube 12 adjacent to its distal end 14, as shown in FIG. 1.

The tracheostomy tube 20 is composed of a medical grade, substantially rigid synthetic material of a type commonly used for such purposes in the medical arts. Radiopaque polyvinyl chloride is one example of a suitable composition. Tracheostomy tube 20 typically possesses a permanent curve along its length which facilitates its introduction into the tracheal wall opening. Tracheostomy tube 20 comprises a distal end 22 having an aperture open to the trachea and lungs of the patient when the device is inserted, as well as an inflatable circumferential cuff 24 positioned adjacent to the distal end 22 of the tracheostomy tube 20. Preferably, the tracheostomy tube is generally cylindrical along its length, and includes a slight distal taper 21 at its distal end as shown in FIG. 1. As is conventional, the tracheostomy tube cuff 24 is desirably a thin wall, high volume, low pressure cuff, composed of a flexible and somewhat elastic material. This permits the cuff 24 to establish a good seal between the tracheostomy tube 20 and the trachea of the patient upon insertion of the tracheostomy tube in well-known fashion.

The tracheostomy tube 20 can further comprise a flange 27 for abutment against the skin of the patient when the tracheostomy tube 20 is inserted in the ostomy. The flange 27 is represented diagrammatically in the Figures as a flat disk, but can of course have other well-known configurations for flanges used in such devices, such as a swivel neck plate. A supply 25 of low-pressure fluid (such as air) for inflating the cuff 24 is also represented schematically in FIG. 1. The nature of such fluid supplies is well known, and need not be further described.

The tracheostomy tube 20 possesses conventional dimensions suited to the patient into whom it will be introduced. For example, for adult patients, the tracheostomy tube can typically have an outside diameter of about 7 to 14 mm, and an inside diameter of about 5 to 10 mm. For pediatric patients, the tracheostomy tube can be made to any smaller dimensions as may be appropriate.

The diameter of the dilator tube 12 is selected in light of the dimensions of the tracheostomy tube 20 being inserted. For example, it is preferable but not essential that the outside diameter of the dilator tube 12 be very close to the inside diameter of the tracheostomy tube 20. Indeed, these two diameters can possess the same nominal value, that is, the dilator tube 12 can have the same 8.5 mm diameter as a nominal 8.5 mm inside diameter of the tracheostomy tube 20. The slight resiliency of the dilator tube 12 permits this close tolerance. When such dimensions are closely matched, those skilled in the art recognize that it may be advantageous to apply a water-soluble jelly or other lubricant over the dilator tube 12, to ensure that the tracheostomy tube 20 may be readily disengaged from the dilator tube once proper placement of the tracheostomy tube has been made.

It is also desirable that the balloon 18, upon inflation, have a diameter at least equal to, and preferably slightly greater than, the outside diameter of the tracheostomy tube 20 and uninflated cuff 24. This close sizing or slight oversizing of the inflated balloon diameter as compared to the tracheostomy tube outer diameter facilitates insertion of the tracheostomy tube 20 into the dilated tracheal wall opening, and minimizes the possibility of damage to the uninflated cuff 24 as it passes through the opening.

As stated above, although not required, in the preferred arrangement the tracheostomy tube 20 is coaxially carried by the dilator tube 12. In this case, the dilator tube 12, balloon catheter 16 and tracheostomy tube 20 are adapted for simultaneous advancement along a wire guide 13, i.e., without longitudinal movement of any of them relative to one another during advancement. Such movement as a single unit reduces the number of manipulative steps necessary to introduce the tracheostomy tube 20 into the opening, thereby making the introduction faster and easier to perform. Following insertion, tracheostomy tube 20 can be taped or strapped to the neck of the patient in any conventional manner.

It should be evident from the above discussion that the device 10 of the present invention can therefore comprise not only the combination of the dilator tube 12 and the balloon catheter 16, but optionally the tracheostomy tube 20. The device can also comprise a conventional wire guide, and if desired, a needle for introducing the device via the well-known Seldinger technique.

During placement of the device utilizing the well-known Seldinger technique, the tip of the wire guide is initially inserted through the tracheal wall via a bore in the needle in well-known fashion. The dilational device 10 (which may or may not include the tracheostomy tube) is advanced along the wire guide until the uninflated balloon 18 lies across the tracheal wall 100. As shown in FIG. 4, uninflated balloon 18 is positioned relative to tracheal wall 100 such that one of the rings 28, 29 is positioned on each side of the wall. This arrangement is shown in FIG. 4.

Once the balloon is properly positioned as shown, the balloon is ready for inflation. The inflation fluid from fluid supply 36 is then pumped or otherwise advanced into the interior space of balloon 18 via port(s) 37 in well-known fashion to the desired inflation limit. As a result, the balloon is inflated (FIG. 5) while it lies across the tracheal wall 100 to atraumatically dilate a portion of the tracheal wall, and thereby form the opening in the wall for insertion of the tracheostomy tube. Rings 28, 29 serve as retention members to retain the position of the balloon 18 across tracheal wall as shown in FIGS. 4 and 5, and thereby minimize a possibility of slippage or otherwise unintended dislodgement of the balloon from its position across the tracheal wall 100 as shown.

Following dilation of the tracheal wall opening, the balloon 18 is deflated by releasing the inflation fluid in the opposite direction from which it was passed into the balloon interior. The tracheostomy tube 20 may then be inserted by advancing the device as shown in FIG. 1 into the opening until tracheostomy tube flange 27 abuts the skin over the tracheal wall. When the tracheostomy tube has been properly placed, the dilator tube 21, balloon catheter 16, and wire guide 13 may be withdrawn, and the tracheostomy tube cuff 24 may be inflated to provide a seal in conventional manner between the tracheal wall and the tracheostomy tube. Alternatively, if the tracheostomy tube is a separate tube not carried by the dilator tube, the dilator tube, balloon catheter, and wire guide may be withdrawn from the opening, and the tracheostomy tube may thereafter be manually inserted into the opening. Further details concerning insertion of a tracheostomy tube are provided in the incorporated-by-reference U.S. Pat. No. 5,653,230.

Although balloon retention rings 28, 29 in FIGS. 1, 2, 4, and 5, are shown as unbroken structures extending around the circumference of the balloon, this is not critical, and other arrangements may be substituted. For example, as shown in FIG. 6, balloon 18 may be equipped with retention structure comprising broken, or segmented, rings 78, 79. In this arrangement, segmented rings 78, 79 may have the same radial extension and axial separation as rings 28, 29. Providing segmented rings, rather than unbroken rings as previously shown, may facilitate manufacture of the balloon. Additionally, providing segmented rings, or "bumps", may better enable the balloon to maintain radial extension of the segments while the balloon is under pressure. When present, the segments need not necessarily be spaced as shown, and those skilled in the art will appreciate that other dimensions and spacing are acceptable in a particular case. Each ring need not have identical segmenting, and as a further alternative, each one of the rings need not be segmented. In other words, if desired, one ring may include segments, and the other ring may be unbroken. For manufacturing purposes, however, it will generally be preferred to have identical rings 28, 29 or 78, 79, whether segmented or unsegmented.

Although the retention structures shown and described above comprise rings (segmented or unsegmented), other shaped and/or positioned retention structure along the surface of the balloon may be substituted, as long as such structures are capable of retaining the balloon in position across the tracheal wall, and thereby minimizing the possibility of slippage or dislodgement of the balloon during inflation and dilation. Regardless of the particular geometric configuration of the separate retention members, at least one such member should be positioned at each side of the tracheal wall, and the members should have sufficient radial strength and dimension to minimize slippage or dislodgement as described.

As another alternative, the balloon may be formed to have a groove or other depression along its outer surface, rather than radially projecting retention members as described above. One example of this arrangement is shown in FIG. 7. In this embodiment, a balloon 80 is formed to have groove 85 formed along the distal portion of the length of balloon 80. Groove 85 has a proximal boundary 86 and a distal boundary 87. Groove 85 will typically be dimensioned such that proximal and distal boundaries 86, 87 are approximately 12-20 mm apart, and more preferably about 15 mm apart. Desirably, each one of boundaries 86, 87 extends slightly beyond the respective borders of the tracheal wall, in the same manner as rings 28, 29 as shown in FIGS. 4 and 5. Preferably, groove 85 is defined by sides 88, 89 that converge to a point 84. Point 84 preferably extends radially inwardly from the outer surface of balloon approximately 1-5, and more preferably, about 2 mm. Thus, for example, when balloon 80 has an outer diameter of 20 mm, the diameter of the balloon at point 84 defined by the inwardly converging sides may be about 16 mm.

Although the groove structure is shown in FIG. 7 as a single groove with converging sides 88, 89 and point 84, those skilled in the art will appreciate that other configurations comprising, e.g., an elongated grooved segment or one or more inward depressions from the outer surface of the balloon may be substituted. The segmented rings and grooves described herein may be formed along the surface of the balloon in the same manner as the ring structures described above, for example, by molding in a suitably-shaped cavity. As a further alternative, the balloon can be provided with both rings and grooves if desired.

Although the device has been described herein in connection with one intended use, that is for dilating an opening through the tracheal wall of a patient, additional uses are contemplated. For example, with minor modification, the device can be adapted for other uses in which dilation of a bodily opening is desirable, followed by positioning an interventional device therein, which other uses are considered within the scope of the invention.

Any undisclosed details of the construction or composition of the various elements of the disclosed embodiment of the present invention are not believed to be critical to the achievement of the advantages of the present invention, so long as the elements possess the strength or flexibility needed for them to perform as disclosed. The selection of these and other details of construction are believed to be well within the ability of one of ordinary skill in the art, in view of the present disclosure.

What is claimed is:

1. A device for dilating an opening through a tracheal wall of a patient, comprising:
   a balloon catheter having a proximal end and a distal end, said balloon catheter including an inflatable balloon at said distal end, said inflatable balloon having an outer surface and being adapted to dilate a portion of the tracheal wall upon inflation, said balloon comprising retention structure along said outer surface such that upon inflation of said balloon said retention structure inhibits a dislodgement of said balloon when positioned across said tracheal wall; and
   a loading dilator, said loading dilator having a distal end and having a lumen extending therethrough, said balloon catheter receivable in said dilator lumen such that said balloon catheter distal end extends distal to said loading dilator distal end;
   wherein said retention structure comprises a pair of spaced elements radially projecting from said balloon outer surface, said elements spaced along said balloon outer surface such that each of said elements is disposed at an opposite side of said tracheal wall when said balloon is inserted into said tracheal wall opening.

2. The device of claim 1, wherein said balloon comprises a flexible and generally inelastic polymer, and said spaced elements comprise said flexible and generally inelastic polymer.

3. The device of claim 1, wherein said spaced elements comprise respective rings disposed at opposite sides of the tracheal wall.

4. The device of claim 3, wherein said rings have a radial extension of about 1-5 mm beyond the outer surface of the balloon.

5. The device of claim 4, wherein said rings are spaced about 15-20 mm along the outer surface of the balloon.

6. The device of claim 1, wherein said spaced elements comprise respective segmented members.

7. A device for dilating an opening through a tracheal wall of a patient, comprising:
   a balloon catheter having a proximal end and a distal end, said balloon catheter including an inflatable balloon at said distal end, said inflatable balloon having an outer surface and being adapted to dilate a portion of the tracheal wall upon inflation, said balloon comprising retention structure along said outer surface such that upon inflation of said balloon said retention structure inhibits a dislodgement of said balloon when positioned across said tracheal wall;
   wherein said retention structure comprises a groove formed along said balloon outer surface, said groove having a proximal boundary and a distal boundary, said boundaries spaced for inhibiting said balloon dislodgement.

8. The device of claim 7, further comprising a loading dilator, said loading dilator having a distal end and having a lumen extending therethrough, said balloon catheter receivable in said dilator lumen such that said balloon catheter distal end extends distal to said loading dilator distal end, and a tracheostomy tube carried by said loading dilator, said tracheostomy tube having a proximal end, a distal end, an outer diameter, and a bore extending longitudinally therethrough, said tracheostomy tube and said balloon catheter aligned such that the distal end of the balloon catheter extends through the tracheostomy tube bore, and a proximal end of the inflatable balloon is distal to the distal end of the tracheostomy tube, said tracheostomy tube adapted to provide an airway through said tracheal wall following said dilation of said wall.

9. The device of claim 8, further comprising a wire guide, said balloon catheter comprising first and second lumens extending therein, said first lumen dimensioned to receive said wire guide, and said second lumen configured for passage of an inflation fluid therethrough to an interior space of said balloon.

10. The device of claim 8, wherein said balloon upon inflation has an outer diameter at least as large as the outer diameter of the tracheostomy tube.

11. A method for dilating an opening through a tracheal wall of a patient, comprising:
   providing a dilation device for said opening, said dilation device comprising a loading dilator having a lumen extending therethrough, and a balloon catheter received in said dilator lumen, said balloon catheter having a distal end extending distal to a distal end of said loading dilator, said balloon catheter including an inflatable balloon at said distal end, said inflatable balloon having an outer surface and being structured to dilate a portion of the tracheal wall upon inflation, said balloon comprising retention structure along said outer surface for inhibiting a dislodgement of said balloon upon inflation when positioned across said tracheal wall, wherein said retention structure comprises a pair of spaced elements radially projecting from said balloon outer surface, and wherein said dilation device having the balloon in the uninflated condition is advanced over the wire guide such that one of said elements is disposed at each side of said tracheal wall prior to inflating said balloon;
   inserting an end of a wire guide through said tracheal wall opening;
   advancing said dilation device having the balloon in an uninflated condition over the wire guide until the balloon retention structure is positioned across the tracheal wall; and
   inflating the balloon to dilate the tracheal wall opening.

12. The method of claim 11, wherein said spaced elements comprise respective rings disposed at opposite sides of the tracheal wall.

13. A method for dilating an opening through a tracheal wall of a patient, comprising:
   providing a dilation device for said opening, said dilation device comprising a loading dilator having a lumen extending therethrough, and a balloon catheter received in said dilator lumen, said balloon catheter having a distal end extending distal to a distal end of said loading dilator, said balloon catheter including an inflatable balloon at said distal end, said inflatable balloon having an outer surface and being structured to dilate a portion of the tracheal wall upon inflation, said balloon comprising retention structure along said outer surface for inhibiting a dislodgement of said balloon upon inflation when positioned across said tracheal wall, wherein said retention structure comprises a grooved segment formed along said balloon outer surface, and wherein said dilation device having the balloon in the uninflated condition is advanced over the wire guide such that at least a length of said grooved segment is disposed along said tracheal wall prior to inflating said balloon;
   inserting an end of a wire guide through said tracheal wall opening;

advancing said dilation device having the balloon in an uninflated condition over the wire guide until the balloon retention structure is positioned across the tracheal wall; and inflating the balloon to dilate the tracheal wall opening.

14. The method of claim 11, further comprising a tracheostomy tube coaxially carried by the loading dilator, wherein the method further comprises: deflating the balloon; and further advancing the dilation device over the wire guide along the dilated tracheal wall opening such that the tracheostomy tube is positioned across the tracheal wall.

15. A device for providing an airway through a tracheal wall of a patient, comprising:
   a loading dilator having an outer surface, a tapered distal end, and having a lumen extending therethrough;
   a balloon catheter having a proximal end and a distal end, said balloon catheter receivable in said dilator lumen such that said balloon catheter distal end extends distal to said loading dilator distal end, said balloon catheter including an inflatable balloon at said distal end, said inflatable balloon having an outer surface and being structured to atraumatically dilate a portion of the tracheal wall upon inflation, said balloon comprising a pair of spaced elements radially projecting from said balloon outer surface, said elements spaced along said balloon outer surface such that each of said elements is disposed at an opposite side of said tracheal wall when said uninflated balloon is inserted into said tracheal wall opening; and
   a tracheostomy tube received on said loading dilator outer surface.

16. The device of claim 15, wherein said balloon is inflatable to a diameter at least as large as a diameter of said tracheostomy tube.

17. The device of claim 15, wherein said spaced elements comprise respective rings spaced about 15-20 mm along said balloon outer surface, said rings having a radial extension of about 1-5 mm beyond the balloon outer surface.

18. The device of claim 1, further comprising a tracheostomy tube carried by said loading dilator, said tracheostomy tube having a proximal end, a distal end, an outer diameter, and a bore extending longitudinally therethrough, said tracheostomy tube and said balloon catheter aligned such that the distal end of the balloon catheter extends through the tracheostomy tube bore, and a proximal end of the inflatable balloon is distal to the distal end of the tracheostomy tube, said tracheostomy tube adapted to provide an airway through said tracheal wall following said dilation of said wall.

19. The device of claim 18, further comprising a wire guide, said balloon catheter comprising first and second lumens extending therein, said first lumen dimensioned to receive said wire guide, and said second lumen configured for passage of an inflation fluid therethrough to an interior space of said balloon.

20. The device of claim 18, wherein said balloon upon inflation has an outer diameter at least as large as the outer diameter of the tracheostomy tube.

* * * * *